(12) United States Patent
Xie

(10) Patent No.: US 12,383,562 B2
(45) Date of Patent: Aug. 12, 2025

(54) APPLICATION OF METAL COMPLEX

(71) Applicant: Hunan Fangshengtai Medical Technology Co., Ltd., Hunan (CN)

(72) Inventor: Fang Xie, Hunan (CN)

(73) Assignee: Shenzhen Fangshengtai Medical Technology Co., Ltd., Shenzhen (CN)

( * ) Notice: Subject to any disclaimer, the term of this patent is extended or adjusted under 35 U.S.C. 154(b) by 855 days.

(21) Appl. No.: 17/622,417

(22) PCT Filed: Jun. 22, 2020

(86) PCT No.: PCT/CN2020/097507
§ 371 (c)(1),
(2) Date: Dec. 23, 2021

(87) PCT Pub. No.: WO2020/259447
PCT Pub. Date: Dec. 30, 2020

(65) Prior Publication Data
US 2022/0370472 A1   Nov. 24, 2022

(30) Foreign Application Priority Data
Jun. 24, 2019 (CN) .......................... 201910547684.X

(51) Int. Cl.
*A61K 31/555* (2006.01)
*A61P 25/04* (2006.01)

(52) U.S. Cl.
CPC ............ *A61K 31/555* (2013.01); *A61P 25/04* (2018.01)

(58) Field of Classification Search
CPC ......... A61K 31/555; A61P 25/04; A61P 25/02
USPC ........................................................ 514/184
See application file for complete search history.

(56) References Cited

FOREIGN PATENT DOCUMENTS

WO      WO 97/47296 A1 * 12/1997   ........... A61K 31/555

\* cited by examiner

*Primary Examiner* — Charanjit Aulakh
(74) *Attorney, Agent, or Firm* — NIXON & VANDERHYE P.C.

(57) ABSTRACT

A drug composition having the structure of formula I for the treatment of pain is provided. The drug can be given to an animal via oral, transdermal, rectal, intravenous, subcutaneous, sublingual or intraperitoneal administration, etc., thereby exerting an analgesic effect. The active components of the drug are convenient to prepare and easy to identify, and are structurally different from those of all other existing analgesic drugs, thus forming a novel class of effective analgesic compounds.

5 Claims, 1 Drawing Sheet

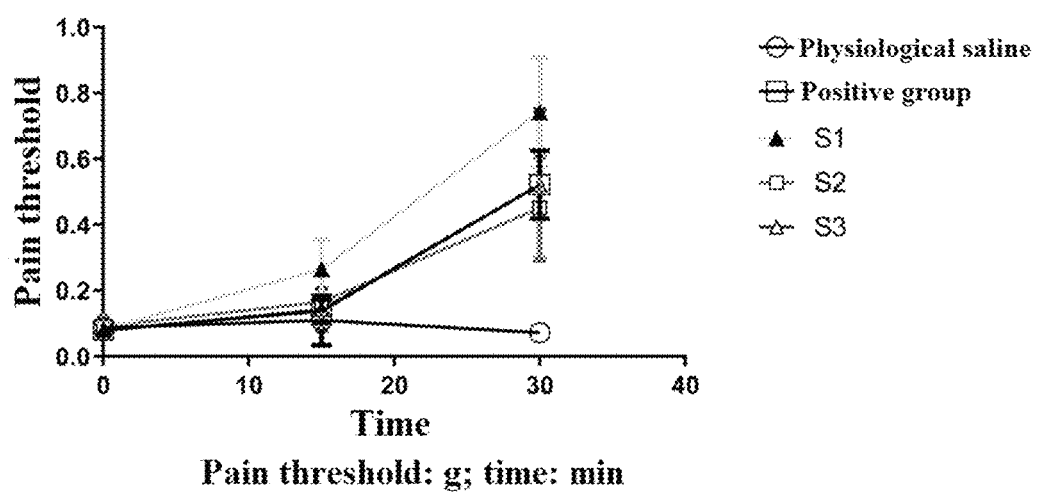

APPLICATION OF METAL COMPLEX

CROSS-REFERENCE TO RELATED APPLICATIONS

This application is a U.S. National Phase of PCT Application No. PCT/CN2020/097507, filed Jun. 22, 2020, which claims the benefit of Chinese Patent Application No. 201910547684.X, filed Jun. 24, 2019, each of which is incorporated herein by reference in its entirety.

TECHNICAL FIELD

The present invention relates to a method and drug composition for the treatment of pain, in particular for the treatment of acute pain, chronic pain, inflammatory pain, cancer pain and a pain caused by cancer treatment, visceral pain, neuropathic pain, a pain caused by diabetic neuropathy, post-herpetic pain, migraine, fibromyalgia, and trigeminal neuralgia.

BACKGROUND

Pain is an unpleasant subjective sensory and emotional experience associated with tissue damage or potential tissue damage. In clinical practice, pain is often the patient's chief complaint. Many pains cause patients' reduced overall capacity, limited mobility, sleep disturbances, and reduced quality of life due to the lack of effective treatment. Also, pain can trigger more serious consequences. According to statistics in 1999, more than two million people lost their mobility every day because of pain [M. Williams, E. A. Kowaluk, and S. P. Arneric, *J. Med. Chem.* 42, 1481-1500 (1999)], such as pains caused by cancer, arthritis, migraine, etc.

There are various types of pain, which can be divided into acute and chronic pain according to the duration of pain, and can be divided into visceral pain, joint pain, muscular pain, migraine and so on according to the occurrence site of pain. Pain can also be classified based on mechanistic considerations, such as inflammatory pain and neuropathic pain. However, it has been proposed in some theory that the essence of neuropathic pain is the inflammation of the nerves and that neuropathic pain is inseparably related to inflammatory pain.

The integrity of the human body is ensured by a coordinated functioning of two major systems: the immune system and the nervous system. In case of a tissue injury, both systems work in concert to cause sensitization of the affected area, with the objective of halting the spread of the damage and ensuring the speedy repair of the damaged area. This process is called inflammation. If inflammation is primarily mediated by the immune system, it is called humoral inflammation, or neurogenic inflammation if it is caused by the nervous system. Sensation of pain caused by inflammation begins with the activation of peripheral terminals of a group of sensorial neurons, also known as nociceptor neurons or nociceptors. Nociceptor neurons convey information about of tissue damage to the processing centers of the sensation of pain in the spinal cord and the brain. (US 2011/0206752 A1 and literatures referred to therein). Once pain is transmitted to the brain and nervous centralis, the nociceptors exert an efferent function, releasing pro-algesic and pro-inflammatory molecules that enhance inflammation and pain, altering the nociceptive excitability or peripheral sensitization, causing changes in the perception of stimuli applied to the damaged area, such as hyperalgesia or allodynia. Persistent excitation of peripheral nociceptors leads to synaptic changes at the level of the spinal cord, leading to a process of central sensitization.

There is a solid biological evidence for the close relationship between the immune system and pain: in both physiological and pathological conditions, peripheral nociceptive neurons may express a variety of immune-related receptors, such as chemokine receptors and immunoglobulin (Fc) receptors that are usually found on immune cells. [T. Wang and C. Ma, *Adv. Exp. Med. Biol.* 904, 77-85 (2016)]. Traditional methods for the treatment of pain are generally divided into four categories: non-steroidal anti-inflammatory drugs (NSAIDs) represented by aspirin and ibuprofen, morphine-based drugs, anticonvulsants and antidepressants. However, all these existing drugs have significant limitations. For example, a non-steroidal anti-inflammatory drug has analgesic ceiling effect, i.e., increasing the dose of a drug can no longer lead to any gain in relief of pain after a certain dose limit is reached; moreover, they may cause intestinal discomfort, and long-term use may also cause gastric ulcers. Another example is that although the morphine-based drugs are widely used, their side effects, such as constipation, reduced respiratory function and addiction, make their doses used in patients strictly under control.

In conclusion, existing drugs are far from meeting the human demands for pain control, especially for the treatment of chronic pain. The development of drugs with new targets is particularly important because the limitations of traditional analgesic drugs are likely due to the limitations of the targets on which they act. The search for analgesic drugs with low side effects and long-lasting effects, or drugs for the radical treatment of pain, is a direction of drug development.

SUMMARY

The present invention provides an analgesic drug composition having a chemical structure shown in formula I, i.e., a metal complex formed by a transition metal ion (e.g., $Zn^{2+}$, $Co^{2+}$, $Pt^{2+}$) or an oxometal ion (e.g., VO(IV), $MoO_2$ (VI)) and a ligand of alpha-hydroxypyranone or alpha-hydroxypyridone type. The metal complex has the characteristic of complexation of two identical alpha-hydroxypyranone or alpha-hydroxypyridone ligands with a transition metal ion or an oxometal ion, wherein the transition metal ion or oxometal ion forms an unsaturated, metal ion-containing five-membered ring with $X_1$ and $X_2$, and the $X_1$ and $X_2$ are heteroatoms. VO(IV) represents

and $MoO_2$ (VI) represents

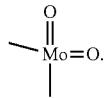

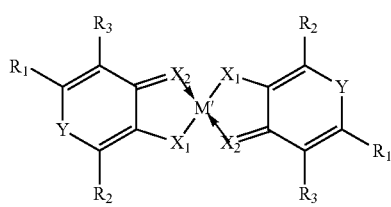

Formula I

Wherein, M'=VO(IV), $Co^{2+}$, $Zn^{2+}$, $MoO_2$(IV) or $Pt^{2+}$; $X_1$=O or S; $X_2$=O or S; Y=O or $NR_4$, and $R_1$, $R_2$, $R_3$ or $R_4$ is H, hydroxyl, mercapto, $C_1$-$C_{14}$ alkyl, hydroxy $C_1$-$C_{14}$ alkyl, $C_1$-$C_{14}$ alkoxy, mercapto $C_1$-$C_{14}$ alkyl, $C_1$-$C_{14}$ alkylthio, aryl or aryl $C_1$-$C_{14}$ alkyl.

The ligands, for forming the metal complexes shown in the formula I, i.e., alpha-hydroxypyranone or alpha-hydroxypyridone type of compounds, can be represented by a formula II. The common feature of these compounds is that the hydroxyl (or mercapto) group is adjacent to a carbonyl (or thiocarbonyl) group.

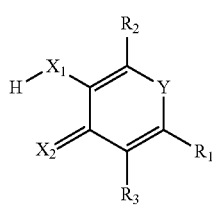

Formula II

Wherein, $X_1$=O or S; $X_2$=O or S; Y=O or $NR_4$, and $R_1$, $R_2$, $R_3$ and $R_4$ are each H, hydroxy, mercapto, hydroxy $C_1$-$C_{14}$ alkyl, $C_1$-$C_{14}$ alkoxy, $C_1$-$C_{14}$ alkyl, mercapto $C_1$-$C_{14}$ alkyl, $C_1$-$C_{14}$ alkylthio, aryl or aryl $C_1$-$C_{14}$ alkyl.

Further optimized metal complexes (as shown in the formula I) formed by a ligand of alpha-hydroxypyranone or alpha-hydroxypyridone type and the above transition metal ion or oxometal ion can be represented by a formula III:

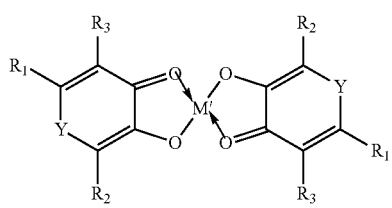

Formula III

Wherein, M'=VO(IV), $Co^{2+}$, $Zn^{2+}$, $MoO_2$(IV) or $Pt^{2+}$; Y=O, $R_1$, $R_2$ and $R_3$ are each hydroxy, mercapto, hydroxy $C_1$-$C_4$ alkyl, $C_1$-$C_4$ alkoxy, mercapto $C_1$-$C_4$ alkyl, $C_1$-$C_4$ alkylthio, phenyl or phenyl $C_1$-$C_4$ alkyl; or Y=$NR_4$, $R_3$=H, $R_1$, $R_2$ and $R_4$ are each hydroxy, mercapto, hydroxy $C_1$-$C_4$ alkyl, $C_1$-$C_4$ alkoxy, mercapto $C_1$-$C_4$ alkyl, $C_1$-$C_4$ alkylthio, phenyl or phenyl $C_1$-$C_4$ alkyl.

Further preferred compounds are the alpha-hydroxypyranone metal complexes shown in a formula IV:

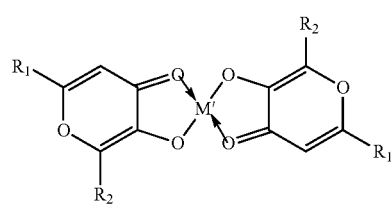

Formula IV

Wherein, M'=VO(IV), $Co^{2+}$, $Zn^{2+}$, $MoO_2$(IV) or $Pt^{2+}$; $R_1$=H, and $R_2$=Me; or $R_1$=H, and $R_2$=—$CH_2CH_3$; or $R_1$=—$CH_2OH$, and $R_2$=H.

The above ligands can be synthesized by conventional chemical synthesis techniques. Metal complexes of these ligands can usually be synthesized by mixing an appropriate metal salt (e.g., $ZnSO_4$, $K_2PtCl_4$, $VOSO_4$, $Co(NO_3)_2$, or $(NH_4)_2Mo_2O_7$, etc.) with a ligand (e.g., maltol, ethyl maltol, or kojic acid, etc.) by a one-pot method, wherein the molecular structure of maltol is as shown in the formula II, wherein $R_1$=$R_3$=H, $R_2$=Me, and $X_1$=$X_2$=Y=O; the molecular structure of ethyl maltol is as shown in the formula II, wherein $R_1$=$R_3$=H, $R_2$=—$CH_2CH_3$, and $X_1$=$X_2$=Y=O; the molecular structure of kojic acid is as shown in the formula II, wherein $R_2$=$R_3$=H, $R_1$=—$CH_2OH$, and $X_1$=$X_2$=Y=O. The following compounds are particularly preferred in the present invention:

bis(maltolato)platinum

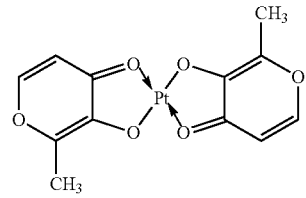

the compound can be prepared according to a method reported in the known literature [see S. D. Kushch, E. N. Izakovich, O. S. Roshchunkina, V. M. Nichvoloda, and M. L. Khidekel, *Bull. Acad. Sci., Div. Chem. Sci.* 30, 681-682 (1981)].

Bis(maltolato)zinc

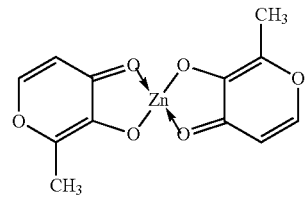

the compound can be prepared according to a method reported in the known literature [see B. S. Parjon-Costa and E. J. Baran, *Spectrochim. Acta Part A: Mol. and Biomol. Spectro.* 113, 337-339 (2013)].

Bis(maltolato)dioxomolybdenum(VI)

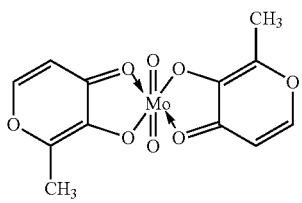

the compound can be prepared according to a method reported in the known literature [see S. J. Greaves and W. P. Griffith. *Polyhedron*, 7, 1973 (1988)].

Bis(5-hydroxy-2-hydroxymethyl-4-pyronato)dioxomolybdenum(VI), Bis(kojato) dioxomolybdenum (VI), $MoO_2(ka)_2$

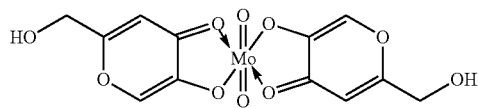

the compound can be prepared according to a method reported in the known literature [see S. J. Lord, N. A. Epstein, R. L. Paddock, C. M. Vogels, T. L. Hennigar, M. J. Zaworotko, N. J. Taylor, W. R. Driedzic, T. L. Broderick, and S. A. Westcott, *Can. J. Chem.* 77, 1249-1261 (1999)].

Bis(maltolato)oxovanadium(IV), $VO(ma)_2$

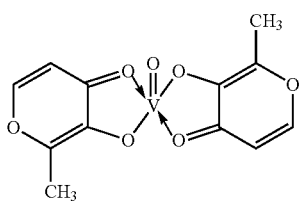

the compound can be prepared according to a method reported in the known literature [see P. Caravan, L. Gelmini, N. Glover, F. G Herring, H. Li, J. H. McNeill, S. J. Rettig, I. A. Setyawati, E. Shuter, Y. Sun, A. S. Tracey, V. G Yuen; and C. Orvig, *J. Am. Chem. Soc.* 117, 12759-12770 (1995)].

Bis(ethylmaltolato)oxovanadium(IV), $VO(ema)_2$

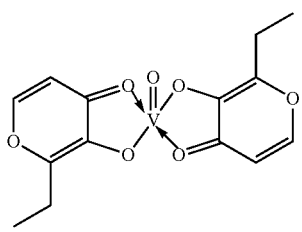

the compound can be prepared according to a method reported in the known literature [see K. H. Thompson, B. D. Liboiron, Y. Sun, K. D. D. Bellman, I. A. Setyawati, B. O. Patrick, V. Karunaratne, G Rawji, J. Wheeler, K. Sutton, S. Bhanot, C. Cassidy, J. H. McNeill, V. G. Yuen, and C. Orvig, *J. Biol. Inorg. Chem.* 8, 66-74 (2003)]

Bis(kojato)oxovanadium(IV), $VO(ka)_2$

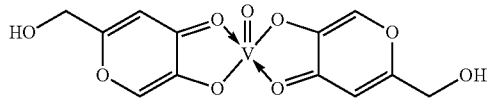

the compound can be prepared according to a method reported in the known literature [see V. G Yuen, P. Caravan, L. Gelmini, N. Glover, J. H. McNeill, I. A. Setyawati, Y. Zbou, and C. Orvig, *J. Inorg. Biochem.* 68, 109-116 (1997)].

Bis(3-hydroxy-1-methyl-2-methyl-4-pyridinonato)oxovanadium(IV), $VO(mmp)_2$

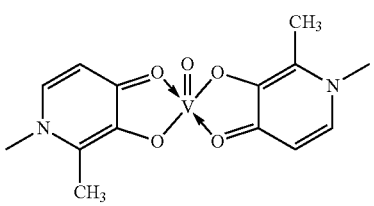

the compound can be prepared according to a method reported in the known literature [see A. Katoh, M. Yamaguchi, K. Taguchi, R. Saito, Y. Adachi, Y. Yoshikawa, and H. Sakurai, *Biomed. Res. Trace Elements* 17, 1-10 (2006) and literature cited herein].

Bis(3-hydroxy-2-methyl-4-pyridinonato)cobalt(II), $Co(mpp)_2$

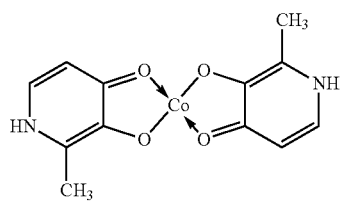

the compound can be prepared according to a method reported in the known literature [see C. Queiros, M. J. Amorim, A. Leite, M. Ferreira, P. Gameiro, B. de Castro, K. Biernacki, A. Magalhães, J. Burgess, and M. Rangel, *Eur. J. Inorg. Chem.* 1131-140 (2011)].

The above compounds may contain 1-20 crystal water or other solvent molecule(s), such as DMSO, ethanol, isopropanol, pyridine, etc.

However, these above compounds, although known, have not been reported in analgesic studies.

The above compounds can be administered orally, and can also be given by other conventional means, such as transdermal, rectal, intravenous, subcutaneous, sublingual, or intraperitoneal administration. The selection of a suitable ligand is based on its backbone and the substituents on the ring.

For oral administration, the so-called "suitability" criterion is the solubility of the overall complex. Preferably, the complex is neutrally charged overall, with a water solubility of at least 0.1 mM and preferably at least 0.2 mM, and orally absorbable (preferably with good gastrointestinal absorption efficiency). The ligand should have a moderate to high complexation capacity (e.g., a binding constant of $2 \leq \log \beta 2 \leq 30$, preferably 5 to 22).

The composition of a pharmaceutical formulation is in a conventional form, for example, capsules, tablets, coated tablets, solutions, suspensions, syrups, suppositories, etc. Adjuvants and excipients of conventional formulations may be used, for example, viscosity modifiers, buffer solutions, flavoring agents, suspending agents, stabilizers, and other additives.

The drug composition of the present invention may include the addition of other agents for treatment, e.g., analgesic agents (e.g., aspirin, etc.), and can also be used in coordination with other analgesic drug(s) for combined treatment or combination therapy.

The metal complex is generally administered at a dose of 0.00001 to 1500 mg (in terms of metal atoms)/kg body weight per day, depending on the subject of administration, its physical condition, and the route of administration. First of all, the dose range is so broad because the effective dose of different mammals is different and they differ significantly from the effective dose in mice, for example, the effective dose in humans can be 10, 20, 30, or even more times lower than the effective dose in mice (per body weight). Mode of administration can also affect the dosage. For example, the oral dosage can be 10 times the injectable dose. For mice, the preferred dose range is 0.01 to 300 mg (in terms of metal atoms)/kg per day. For humans, the preferred dose range is 0.00005 to 5 mg (in terms of metal atoms)/kg per day. Drug unit dose is 0.001 mg to 1000 mg (in terms of metal atoms), preferably 0.1 mg to 300 mg (in terms of metal atoms).

BRIEF DESCRIPTION OF THE DRAWINGS

FIG. 1 is a graph showing the pain-inhibiting effects of bis(maltolato)oxovanadium (S1), bis(ethylmaltolato)oxovanadium (S2) and bis(kojato)oxovanadium (S3), wherein the horizontal coordinate represents time and the vertical coordinate represents pain threshold; the analgesic drug used in the positive control group is aspirin.

DETAILED DESCRIPTION

Drug Analgesic Activity Experiments

The analgesic assays of three vanadium compounds (bis(maltolato)oxovanadium, bis(ethylmaltolato)oxovanadium, and bis(kojato)oxovanadium) in mice are presented below. Some of the results are shown in FIG. 1, where S1 is bis(maltolato)oxovanadium, S2 is bis(ethylmaltolato)oxovanadium, S3 is bis(kojato)oxovanadium, and thepositive group (i.e., a positive control group) is aspirin group.

10 μl of complete Freund's adjuvant (CFA) was injected subcutaneously into the plantar surface of the left hindpaws of mice (♂ Kunming mice, 22-40 g) to produce inflammation. Von Frey tests were performed at 24 hours after injection or later to determine pain thresholds, i.e., under the guidance of a Dixon's Up-Down method, mice were induced with Von Frey fibers to have mechanical withdrawal of their hindpaws data were collected, and their 50% paw withdrawal thresholds (referred to as paw withdrawal threshold or PWT), namely the pain thresholds, were calculated. Afterwards, the mice were divided into a physiological saline group, a positive control group and a drug group, and injected intraperitoneally with 0.4 ml of physiological saline, 0.4 ml of aspirin (acetylsalicylic acid, or ASA) Tris-buffer solution at a concentration of 20 mg/ml and a mixed solution of a tested compound and 0.4 ml of cellulose solution (1%), respectively. Then, changes in the pain threshold were monitored with the Von Frey tests.

Experiment 1: Analgesic Activity Test of bis(maltolato)oxovanadium(IV) (VO(ma)$_2$)

The source of bis(maltolato)oxovanadium(IV) (VO(ma)$_2$): synthesized using a literature method or purchased from Shanghai Dibai Chemical Technology Co. Ltd. After intraperitoneal administration at a dose of 9 mg/kg (approximately 0.03 mmol/kg), all seven mice showed a response to the compound with a general increase in pain threshold.

Experiment 2: Analgesic Activity Test of bis(ethylmaltolato)oxovanadium(IV) (VO(ema)$_2$)

The source of bis(ethylmaltolato)oxovanadium(IV) (VO(ema)$_2$): synthesized using a literature method or purchased from Hubei Hongxin Ruiyu Fine Chemical Co. Ltd. After intraperitoneal administration at a dose of 10 mg/kg (approximately 0.03 mmol/kg), all seven mice showed a response to the compound with a general increase in pain threshold.

Experiment 3: Analgesic Activity Test of bis(kojato)oxovanadium(IV) (VO(ka)$_2$)

The source of bis(kojato)oxovanadium(IV) (VO(ka)$_2$): synthesized using a literature method.

After intraperitoneal administration at a dose of 11 mg/kg (approximately 0.03 mmol/kg), all seven mice showed a response to the compound with a general increase in pain threshold.

The mice showed a significant decrease in the paw withdrawal threshold (FIG. 1) at 24 hours after the injection of CFA, which was manifested as mechanical hyperalgesia, indicating the development of inflammatory pain. At this time, the drugs, i.e., bis(maltolato)oxovanadium (S1 in FIG. 1), bis(ethylmaltolato)oxovanadium (S2 in FIG. 1), or bis(kojato)oxovanadium (S3 in FIG. 1), were injected, and a significant increase in the paw withdrawal threshold was found in mice with inflammatory pain. At 30 min after administration, S1, S2 or S3 increased the paw withdrawal threshold in mice with inflammatory pain from (0.072±0.0076) to (0.74±0.17) (P<0.01, n=7), (0.45±0.15) (P<0.01, n=7) and (0.52±0.23) (P<0.01, n=7), respectively, demonstrating a similar or stronger analgesic effect than that of aspirin.

The invention claimed is:

1. A method of treating pain in a subject suffering from pain comprising administering a pharmaceutical composition comprising a compound of formula IV to the subject:

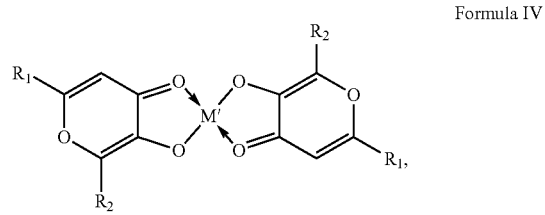

Formula IV wherein, M'=VO(IV), $R_1$=H, and $R_2$=Me; or $R_1$=H, and $R_2$=—CH$_2$CH$_3$; or $R_1$=—CH$_2$OH, and $R_2$=H.

2. The method of claim 1, wherein the compound of formula IV is selected from the following compounds:

bis(maltolato)oxovanadium

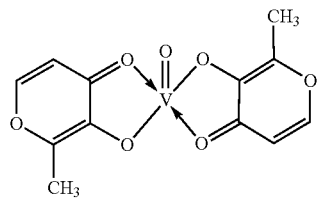

bis(maltolato)oxovanadium

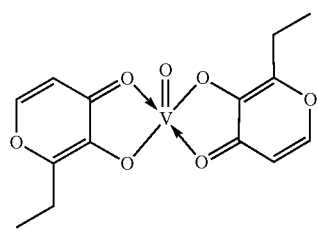

bis(ethylmaltolato)oxovanadium

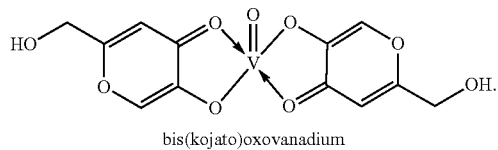

bis(kojato)oxovanadium

3. The method of claim 1, wherein the compound of formula IV is bis(maltolato)oxovanadium

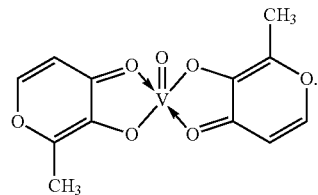

4. The method of claim 1, wherein the compound of formula IV is bis(ethylmaltolato)oxovanadium

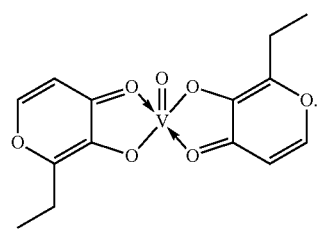

5. The method of claim 1, wherein the compound of formula IV is bis(kojato)oxovanadium

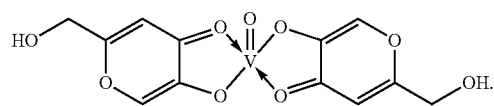

* * * * *